United States Patent

Yeo et al.

Patent Number: 5,541,175
Date of Patent: Jul. 30, 1996

[54] CEPHALOSPORIN ANTIBIOTICS

[75] Inventors: Jae H. Yeo; Chan S. Bang; Jong C. Lim; Young M. Woo; Deog H. Yang, all of Youseong-ku; Se H. Kim; Jae H. Jeon, both of Seoul; Mu Y. Kim, Youseong-ku; Sam S. Kim, Youseong-ku; Tae H. Lee, Youseong-ku; Yong Z. Kim, Youseong-ku; Hun S. Oh, Youseong-ku, all of Rep. of Korea

[73] Assignee: Lucky, Ltd., Seoul, Rep. of Korea

[21] Appl. No.: 301,619

[22] Filed: Sep. 7, 1994

[30] Foreign Application Priority Data

Sep. 11, 1993 [KR] Rep. of Korea ............... 93-18321

[51] Int. Cl.$^6$ .................. C07D 501/60; A01K 31/545
[52] U.S. Cl. ........................... 514/202; 540/222
[58] Field of Search ................ 540/222; 514/202

[56] References Cited

U.S. PATENT DOCUMENTS 5,373,001 12/1994 Aszodi et al. ............... 514/202

Primary Examiner—John M. Ford
Attorney, Agent, or Firm—Birch, Stewart Kolasch & Birch, LLP

[57] ABSTRACT

The present invention relates to a cephalosporin compound represented by the following general formula (I):

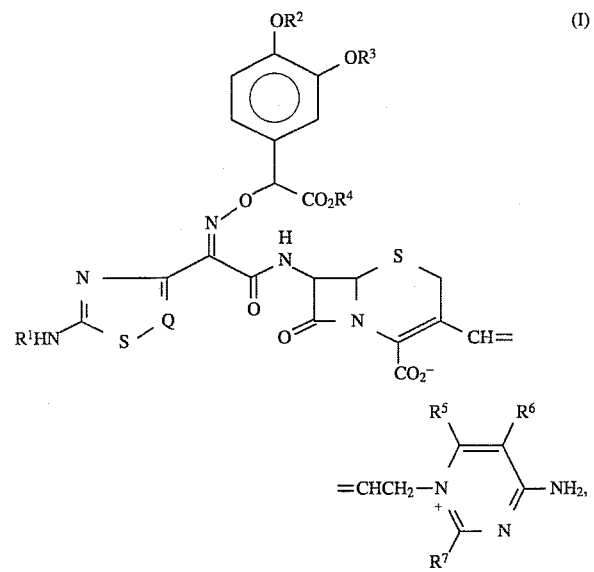

its pharmaceutically acceptable non-toxic salt, physiologically hydrolyzable ester, hydrate or solvate, or isomers thereof, in which $R^1$ represents hydrogen or an amino-protecting group, $R^2$ and $R^3$ can be identical or different and independently of one another represent hydrogen or a hydroxy-protecting group, or $R^2$ and $R^3$ together can form a cyclic diol-protecting group, $R^4$ represents hydrogen or a carboxyl-protecting group, $R^5$, $R^6$ and $R^7$ independently of one another represent hydrogen, amino or substituted amino, hydroxy, alkoxy, $C_{1-4}$ alkyl, carboxyl or alkoxycarbonyl, or $R^5$ and $R^6$ together with the carbon atoms to which they are attached can form a $C_{3-7}$ cycle, and Q represents CH or N, and to a process for preparation thereof and a pharmaceutical composition containing the compound (I) as an active ingredient.

4 Claims, No Drawings

CEPHALOSPORIN ANTIBIOTICS

BACKGROUND OF THE INVENTION

1. Field of the Invention

The present invention relates to a novel cephalosporin compound which is useful as an antibiotic agent. More particularly, the present invention relates to a cephem compound having (Z)-2-(2-aminothiazol(or aminothiadiazol)-4-yl)-2-(α-carboxy-3,4-substituted benzyloxyimino)acetamido group on 7β-position and, at the same time, a 3-substituted propenyl group on C-3 position, that is, a cephalosporin compound represented by the following general formula (I), having an 4-amino-trisubstituted pyrimidinium substituent on 3-position of propenyl group:

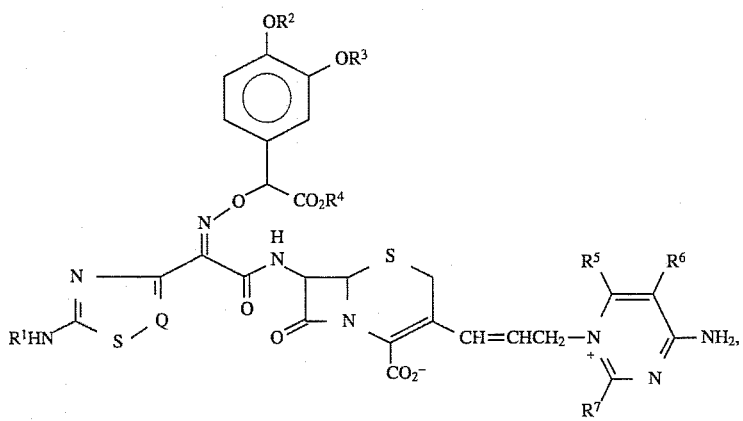

(I)

in which

R$^1$ represents hydrogen or an amino-protecting group,

R$^2$ and R$^3$ can be identical or different and independently of one another represent hydrogen or a hydroxy-protecting group, or R$^2$ and R$^3$ together can form a cyclic diol-protecting group, R$^4$ represents hydrogen or a carboxyl-protecting group, R$^5$, R$^6$ and R$^7$ independently of one another represent hydrogen, amino or substituted amino, hydroxy, alkoxy, C$_{1-4}$ alkyl, carboxyl or alkoxycarbonyl, or R$^5$ and R$^6$ together with the carbon atoms to which they are attached can form a C$_{3-7}$ cycle, and Q represents CH or N, and its pharmaceutically acceptable non-toxic salt, physiologically hydrolyzable ester, hydrate and solvate, and isomers thereof, which have a potent antimicrobial activity and a broad antibacterial spectrum.

The present invention also relates to a process for preparation of the compound of formula (I), as defined above, and to a pharmaceutical composition containing the compound of formula (I) as an active ingredient.

2. Background Art

Cephalosporin antibiotics have been widely used for treatment of diseases caused by pathogenic bacteria in human and animals and are particularly useful for treatment of diseases caused by bacteria which are resistant to other antibiotics such as penicillin compounds and for treatment of penicillin-hypersensitive patients. In most bacterial infections, it is preferable to use antibiotics which are active against both of gram-positive and gram-negative microorganisms. In addition, it has been well known that an antimicrobial activity of such cephalosporin antibiotics is greately influenced by the substituent on 3- or 7-position of the cephem nucleus. Accordingly, it has been attempted to develop an antibiotic compound which shows a high antibacterial activity against a broad range of gram-positive and gram-negative strains and is very stable to β-lactamase produced by various gram-negative bacterial strains and is also very stable in the living body. As a result, heretofore, numerous cephalosporin antibiotics having various substituents on the 7β-acylamido group and the 3-position of cephem nucleus have been developed.

For example, British Patent No. 1,399,086 broadly and generally describes a cephalosporin derivative represented by the following general formula (A):

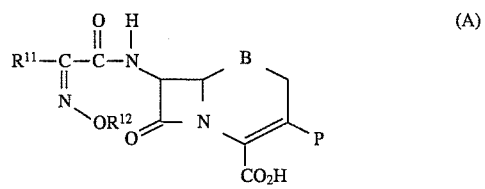

(A)

in which

R$^{11}$ represents hydrogen or an organic group,

R$^{12}$ represents a monovalent etherified organic group which is linked with oxygen atom via carbon atom, B represents —S— or >S→O, and P represents an organic group.

Since the development of the above compounds it has been continuously attempted to develop an antibiotic compound having an improved antibacterial activity particularly against gram-negative strains. As a result of such attempts, British Patent No. 1,522,140 discloses a cephalosporin antibiotic compound represented by the folowing general formula (B), wherein the compound is present as a syn-isomer or a mixture of syn- and anti-isomers containing at least of 90% of syn-isomer:

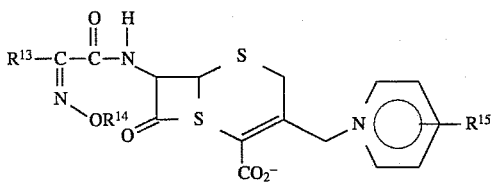

(B)

in which

R$^{13}$ represents furyl or thienyl group, $R^{14}$ represents $C_{1-4}$ alkyl, $C_{3-4}$ cycloalkyl, furylmethyl or thienylmethyl group, and $R^{15}$ represents hydrogen, carbamoyl, carboxymethyl, sulfonyl or methyl group.

Subsequently, numerous studies have been made to develop an antibiotic compound having an improved antibacterial activity against gram-positive strains as well as against gram-negative strains and having a broad antibacterial spectrum. As a result thereof, numerous cephalosporin compounds having a structure similar to that of formula (B) above have been developed. Such development has induced various changes including the introduction of acylamido group into 7-position and a specific group into C-3 position in the cephem nucleus of formula (B).

For example, Belgian Patent No. 852,427 discloses a cephalosporin antibiotic compound which is derived from the compound of formula (A) by replacing $R^{11}$ with various other organic groups such as 2-aminothiazol-4-yl group and attaching the oxygen atom of oxyamino group to an aliphatic hydrocarbon group which, in turn, can be substituted with carboxy group. In this compound, the substituent on C-3 position may be acyloxymethyl, hydroxymethyl, formyl, optionally substituted heterocyclic thiomethyl, and the like.

The compounds described in the above-mentioned patents are totally distinguished from the compounds of the present invention in their structures.

Recently, many efforts have been made to find out compounds having a potent antibacterial activity against a broad range of pathogenic organisms including some gram-negative bacterial strains which produce β-lactamase. One attempt is to introduce a specific group, for example, various heterocyclic groups, aryl, or alkylsulfonylacyl, aryl or aralkyl groups, into C-7 position, particularly into $R^{12}$ position in the compound of formula (A) wherein $R^{11}$ is 2-aminothiazol-4-yl group. As a result, it has been identified that the cephem compounds wherein $R^{12}$ is α-carboxy-3,4-substituted benzyl group show a potent antibacterial activity against broad range pathogenic organisms. Such cephem compounds have been disclosed in many patents such as PCT/JP86/00140, European Patent Application No. 87312525.2, etc.

Specifically, PCT/JP86/00140 discloses a cephem compound having the following general formula (C):

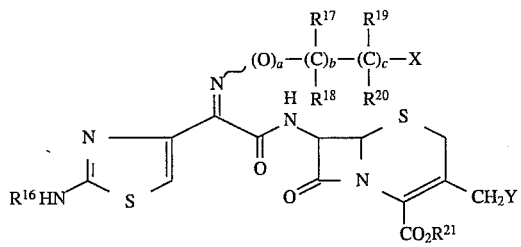

in which $R^{16}$ represents hydrogen or an amino-protecting group, $R^{17}$ and $R^{18}$ represent hydrogen, methyl, carboxyl, protected carboxyl or oxygen atom, $R^{19}$ and $R^{20}$ represent hydrogen or oxygen atom, $R^{21}$ represents hydrogen or a carboxyl-protecting group, a, b and c are an integer of 0 or 1, and X represents hydrogen, hydroxyl or a group of formula

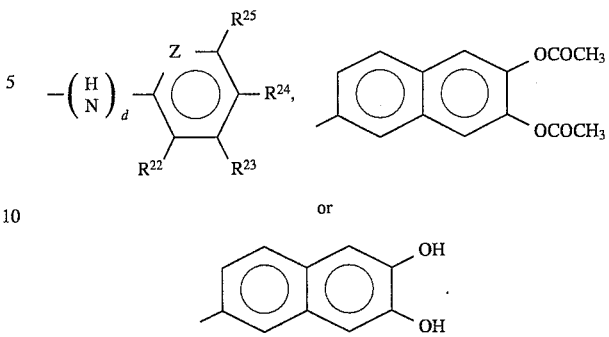

The specification of the above PCT application broadly describes the compounds so that the 7β-position substituent may include (Z)-2-(2-aminothiazol-4-yl)-2-(α-carboxyl-3,4-substituted benzyloxyimino)acetamido group as described in the present invention. However, the structure of this compound is different from that of the compound of the present invention because in the moiety —$CH_2Y$ present on C-3 position the hetero atom (S or N) of Y is bound to C-3 position of cephem nucleus via methylene bridge whereas in the compound of the present invention the hetero atom in the corresponding moiety is bound to the cephem nucleus via propenyl bridge. Furthermore, in the above patent application, although Y can represent some substituted pyridine groups, there is no mention or suggestion on the substituted pyrimidine group as described in the present invention.

In addition, European Patent Application No. 87308525.2 describes the cephem compound represented by the following general formula (D):

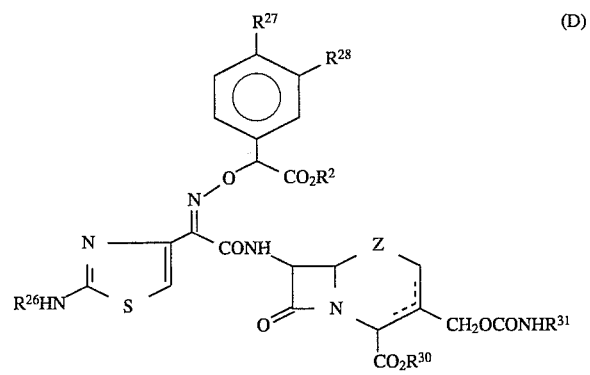

in which $R^{26}$ represents hydrogen or an amino-protecting group, $R^{27}$ and $R^{28}$ independently of one another represent hydroxy or substituted hydroxy, or $R^{27}$ and $R^{28}$ together can form a protected cyclic diol group, $R^{29}$ and $R^{30}$ represent hydrogen or a carboxyl-protecting group, $R^{31}$ represents hydrogen or $C_{1-3}$ alkyl group substituted with 1 to 3 halogen atom(s), Z represents >S or >S→O, and a dotted line denotes 2-cephem or 3-cephem compound.

However, the substituent introduced into C-3 position in the above European patent is different from the C-3 substituent in the compound of the present invention.

Further, European Patent No. 264,091 discloses the cephem compounds haing the following general formula (E):

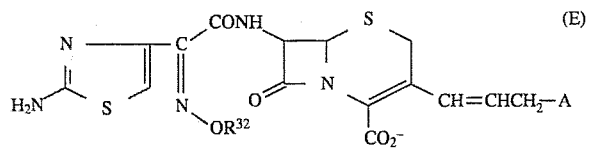

in which

R³² represents lower alkyl group substituted with fluoro, or lower alkyl group substituted with cyano group, and A represents a cyclic or acyclic ammonio group.

The above patent discloses several cyclic ammonio groups as an example of A. However, there is no mention or suggestion on the pyrimidyl group as described in the present invention. Furthermore, the structure of 7-β substituent in the compound of this patent is also different from that in the compound of the present invention.

On the basis of the above-mentioned prior art, the present inventors have extensively and continuously studied to develop a cephalosporin compound having a potent antibacterial activity against broad range of pathogenic microorganisms including β-lactamase producing gram-negative bacteria strains and also having an improved pharmacokinetic property. As a result, we have identified that a certain cephalosporin compound having (Z)- 2-(2-aminothiazol(or aminothiadiazol)-4-yl)-2-(α-carboxy-3,4-substituted benzyloxyimino)acetamido group on 7-β position and, at the same time, an optionally substituted pyrimidinopropenyl group on C-3 position satifies the above-mentioned purpose. Thus, now we have completed the present invention.

Therefore, it is an object of the present invention to provide a novel cephalosporin compound having the general formula (I), as defined above, which has a potent antimicrobial activity, broad antibacterial spectrum and improved pharmacokinetic properties.

It is a further object of the present invention to provide a process for preparing the novel cephalosporin compound of formula (I).

Further, it is another object of the present invention to provide a pharmaceutical composition containing the novel cephalosporin compound of formula (I) as an active ingredient.

The foregoing has outlined some of the more pertinent objects of the present invention. These objects should be construed to be merely illustrative of some of the more pertinent features and applications of the invention. Other many beneficial results can be obtained by applying the disclosed invention in a different manner of modifying the invention within the scope of the disclosure. Accordingly, other objects and a more thorough understanding of the invention may be had by referring to the disclosure of invention, in addition to the scope of the invention defined by the claims.

DISCLOSURE OF INVENTION

In one aspect, the present invention relates to provide a novel cephalosporin compound represented by the following general formula (I):

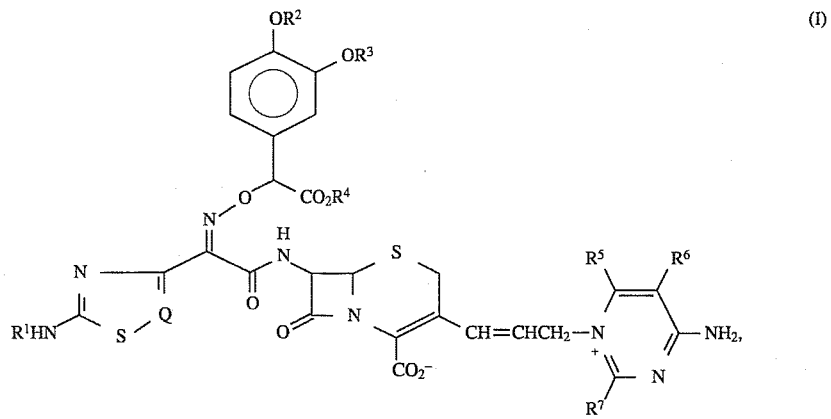

in which $R^1$ represents hydrogen or an amino-protecting group, $R^2$ and $R^3$ can be identical or different and independently of one another represent hydrogen or a hydroxy-protecting group, or $R^2$ and $R^3$ together can form a cyclic diol-protecting group, $R^4$ represents hydrogen or a carboxyl-protecting group, $R^5$, $R^6$ and $R^7$ independently of one another represent hydrogen, amino or substituted amino, hydroxy, alkoxy, $C_{1-4}$ alkyl, carboxyl or alkoxycarbonyl, or $R^5$ and $R^6$ together with the carbon atoms to which they are attached can form a $C_{3-7}$ cycle, and Q represents CH or N, and its pharmaceutically acceptable non-toxic salt, physiologically hydrolyzable ester, hydrate and solvate, and isomers thereof.

The definition of $R^1$ to $R^7$ in the above formula (I) will be more specifically described in the following. The most preferred example of $R^1$ and $R^4$ is hydrogen; and $R^2$ and $R^3$ can be identical or different and are most preferably hydrogen or acetyl. The preferred example of $R^5$ is hydrogen or amino; the preferred example of $R^6$ and $R^7$ independently of one another is hydrogen, amino or methyl; and the preferred example of a cycle which can be formed by $R^5$ and $R^6$ together with the carbon atoms to which they are attached is cyclopentane or cyclohexane.

Since in the formula (I) above, the carbon atom to which a 3,4-substituted phenyl group is attached is an asymmetric center, the compound of formula (I) can be present as a diastereomeric isomer. Accordingly, it should be understood that the present invention includes individual diastereomeric isomer of the compound (I) and the mixture thereof. In addition, the compound of formula (I) according to the present invention can form a tautomeric isomer which is also included within the scope of the present invention. Further, the present compound of formula (I) can be present in the form of a cis- or trans-geometric isomer depending on the geometric configuration of a double bond in the propenyl group as a part of the C-3 substituent. Accordingly, the present invention also includes such geometric isomers and their mixture.

The compound of formula (I) according to the present invention can be present as geometric isomers including syn-isomer or a syn- and anti-isomeric mixture containing 90% or more of syn-isomer. The hydrate and solvate of the compound of formula (I) are also included within the scope of the present invention. In addition, when in the compound of formula (I) Q is CH, since the aminothiazole group can be present as a tautomeric isomer with the aminothiazoline group, such tautomer can also be included within the scope of the present invention:

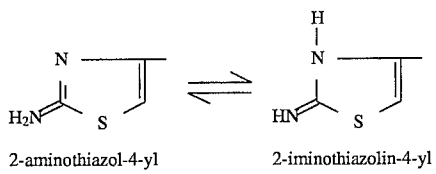

2-aminothiazol-4-yl      2-iminothiazolin-4-yl

When Q denotes N, the aminothiadiazole group can be present as a tautomeric isomer with the iminothiadiazoline group. Such tautomeric isomers are also oncluded within the scope of the present invention:

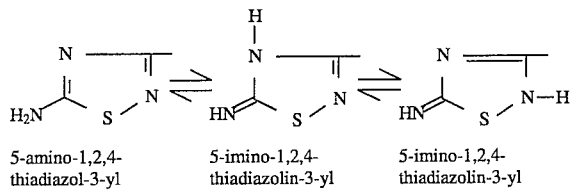

5-amino-1,2,4-     5-imino-1,2,4-     5-imino-1,2,4-
thiadiazol-3-yl    thiadiazolin-3-yl  thiadiazolin-3-yl In addition, depending on the geometric configuration of a double bond in the propenyl group as a part of the C-3 substituent the compound of formula (I) can be present as the following cis- and trans-isomers:

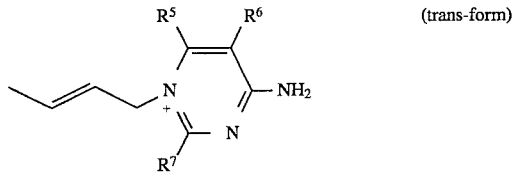

(trans-form)

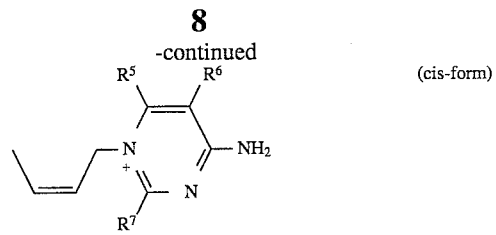

(cis-form)

Such individual geometric isomer and the mixture thereof are also included within the scope of the present invention. However, in view of their antibacterial activities, the trans-isomer is more preferable.

The pharmaceutically acceptable non-toxic salt of the compound of formula (I) includes salts with inorganic acids such as hydrochloric acid, hydrobromic acid, phosphoric acid, sulfuric acid, etc., salts with organic carboxylic acids such as acetic acid, trifluoroacetic acid, citric acid, formic acid, maleic acid, oxalic acid, succinic acid, benzoic acid, tartaric acid, fumaric acid, mandelic acid, ascorbic acid, malic acid, etc., or salts with sulfonic acids such as methanesulfonic acid, paratoluenesulfonic acid, etc., and the like salts, with other acids which are conventionally used in penicillin and cephalosporin fields. These acid addition salts are prepared according to a conventional technique. In addition, the compound of formula (I) can also form a non-toxic salt with base. The base which can be used for this purpose includes inorganic bases such as alkali metal hydroxides, bicarbonates or carbonates (for example, sodium hydroxide, potassium hydroxide, sodium hydrogen carbonate, potassium hydrogen carbonate, sodium carbonate, potassium carbonate, etc.) and alkali earth metal hydroxides or carbonates (for example, calcium hydroxide, calcium carbonate, etc.), or organic bases such as amino acids.

The physiologically hydrolyzable ester of the compound of formula (I) includes, for example, indanyl, phthalidyl, methoxymethyl, pivaloyloxymethyl, glycyloxymethyl, phenylglycyloxymethyl, 5-methyl-2-oxo-1,3-dioxolan-4-yl methyl ester, and other physiologically hydrolyzable esters which are conventionally used in the technical field of penicillins and cephalosporins. Such esters can be prepared according to the known method.

In another aspect, the present invention provides a process for preparing the compound of formula (I). According to the present invention, the compound of formula (I):

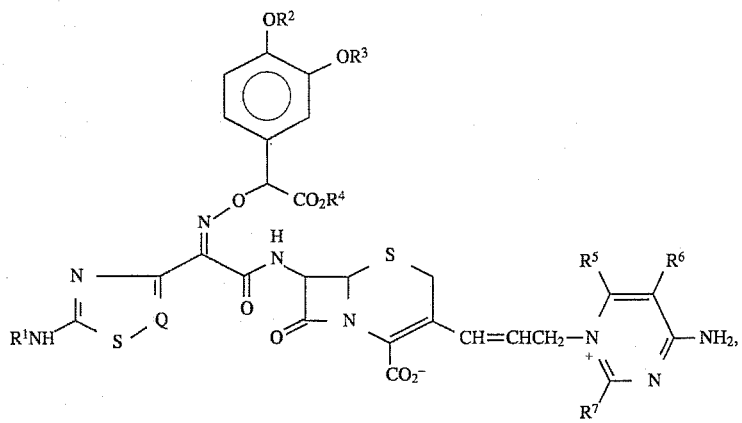

(I)

in which $R^1$ to $R^7$ and Q are defined as previously described, its pharmaceutically acceptable non-toxic salts, its physiologically hydrolyzable esters, hydrates or solvates can be prepared by a process characterized in that a compound having the following general formula (II):

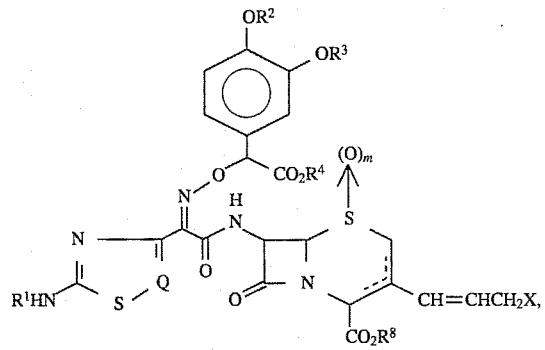

(II)

in which $R^1$ to $R^4$ and Q are defined as previously described, $R^8$ represents hydrogen or a carboxyl-protecting group, X represents halogen and m denotes 0 or 1, is reacted with a compound having the following general formula (III):

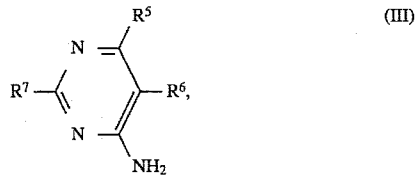

(III)

in which $R^5$, $R^6$ and $R^7$ are defined as previously described, in the presence of a solvent and, if required, before or after reaction the amino-protecting gorup or the carboxyl-protecting group is removed or the S-oxide [S→(O)m] is reduced.

In the above formulae, the amino-protecting group for $R^1$ means a conventional amino-protecting group such as acyl, substituted or unsubstituted ar(lower)alkyl (e.g. benzyl, diphenylethyl, triphenylmethyl, 4-methoxybenzyl, etc.), halo(lower)alkyl (e.g. trichloromethyl, trichloroethyl, etc.), tetrahydropyranyl, substituted phenylthio, substituted alkylidene, substituted aralkylidene, substituted cyclodene, etc. Suitable acyl group as the amino-protecting group may be aliphatic and aromatic acyl groups or acyl groups having heterocyclic ring. Example of such acyl groups may include $C_{1-5}$ lower alkanoyl (e.g. formyl, acetyl, etc.), $C_{2-6}$ alkoxycarbonyl (e.g. methoxycarbonyl, ethoxycarbonyl, etc.), lower alkylsulfonyl (e.g. methylsulfonyl, ethylsulfonyl, etc.), or ar(lower)alkoxycarbonyl (e.g. benzyloxycarbonyl, etc.), and the like. The above-mentioned acyl groups can contain suitable substituents selected from 1 to 3 halogen, hydroxy, cyano, nitro and the like. In addition, the reaction product of amino group with silane, borane or phosphorus compound may also act as the amino-protecting group.

As the carboxyl-protecting group for $R^4$ and $R^8$, any of the conventional groups which can be readily removed under mild condition can be suitable. Specific example thereof includes (lower)alkyl ester (e.g. methyl ester, t-butyl ester, etc.), (lower)alkenyl ester (e.g. vinyl ester, allyl ester, etc.), (lower)alkoxy(lower)alkyl ester (e.g. methoxymethyl ester, etc.), (lower)alkylthio(lower)alkyl ester (e.g. methylthiomethyl ester, etc.), halo(lower)alkyl ester (e.g. 2,2,2-trichloroethyl ester, etc.), substituted or unsubstituted aralkyl ester (e.g. benzyl ester, p-nitrobenzyl ester, p-methoxybenzyl ester, etc.) or silyl ester, and the like.

The hydroxy-protecting group for $R^2$ and $R^3$ may include acyl group [for example, formyl or a —$COR^a$ group wherein $R^a$ is $C_{1-8}$ alkyl, for example, acetyl], alkoxycarbonyl group [for example, a —$CO_2R^a$ (wherein $R^a$ is $C_{1-8}$ alkyl)], silyl group [for example, ($C_{1-4}$ alkyl)silyl such as trimethylsilyl or t-butyldimethylsilyl], or a borate [—$B$=$(OR^b)$] or phosphate [—$P(O)(OR^b)_2$] group (wherein $R^b$ is $C_{1-4}$ alkyl); and the cyclic diol-protecting group which can be formed by $R^2$ and $R^3$ includes $C_{1-7}$ alkylidenedioxy group (for example, methylenedioxy, ethylenedioxy or isopropylidenedioxy), alkylidenedioxy group containing one or more substituent(s) (for example, methoxymethylenedioxy, diphenylmethylenedioxy or carbonyldioxy), cyclic borate group (for example, —OB(OH)O—), cyclic phosphate group (for example, —OP(O)(OH)O— or —OP(O)($OR^b$)O— wherein $R^b$ is defined as previously described) or di($C_{1-4}$ alkyl) silyldioxy group (for example, dimethylsilyldioxy), and the like.

The above-mentioned amino-protecting group, hydroxy-protecting group, cyclic diol-protecting group and carboxyl-protecting group can be readily removed by hydrolysis, reduction, etc., under mild condition to form free amino, hydroxy or carboxyl group and are appropriately selected depending on the chemical properties of the compound of formula (I).

Leaving group X represents halogen such as chloro, fluoro, iodo, etc.

The dotted line in the structure of formula (II) means that the compound of formula (II) can present as each of the compound of formula (II-a) or the compound of formula (II-b) or as a mixture of the compound of formula (II-a) and the compound of formula (II-b):

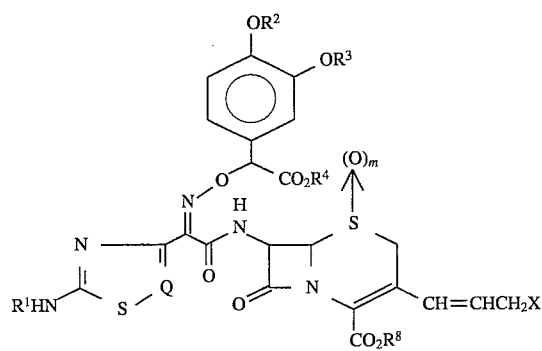

(II-a)

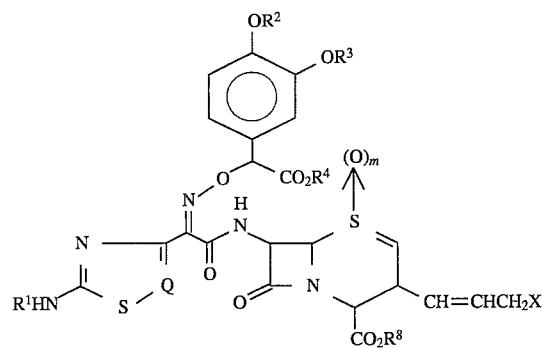

(II-b)

in which $R^1$ to $R^4$, $R^8$, m, Q and X are defined as previously described.

The starting compound of formula (II) used in the present invention can be prepared according to the following reaction scheme. That is, the compound of fomrula (II) can be prepared by activating a compound having the following general formula (IV) or a salt thereof with an acylating agent, reacting the activated compound with a compound of formula (V) to obtain a compound of formula (VI) and then introducing a 3-halogenated propenyl group into the C-3 position of the compound of formula (VI):

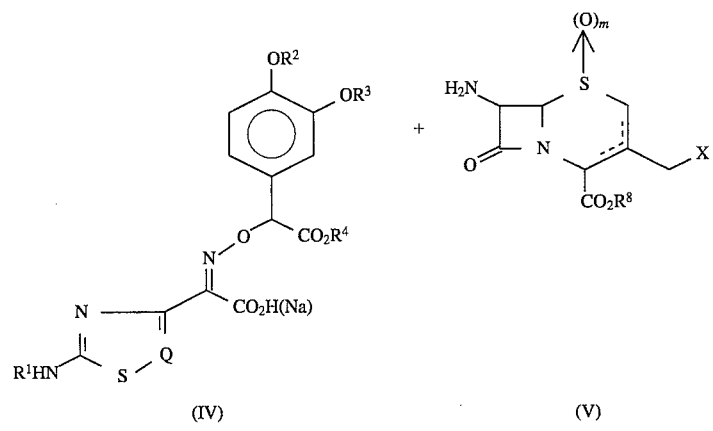

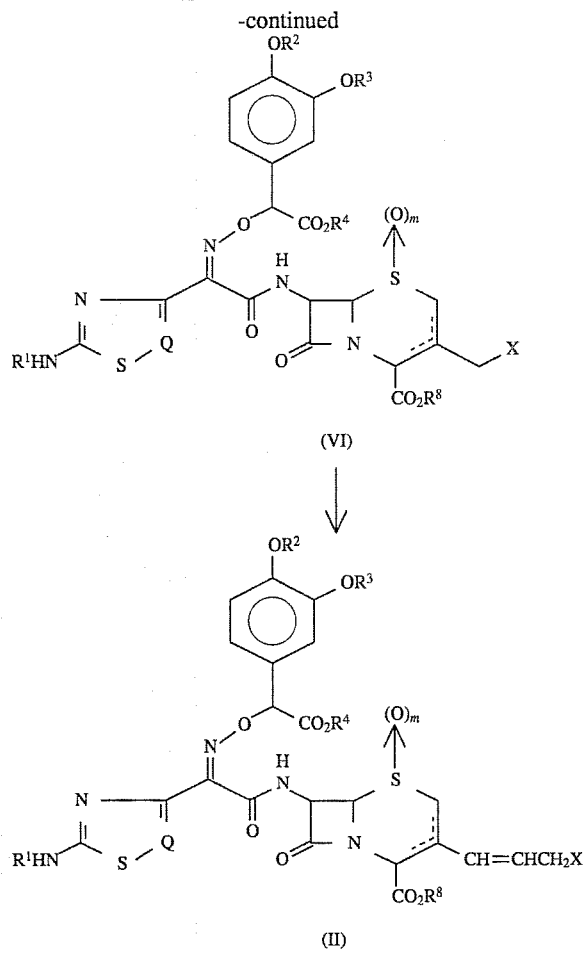

In the above reaction scheme, $R^1$ to $R^4$, $R^8$, m, Q and X are defined as previously described.

The dotted line in the structure of formulae (V) and (VI) and of formulae (VII) and (VIII) as described in the following means that the respective compound can present as 2-cephem or 3-cephem compound or as the mixture thereof.

In preparing the compound of formula (VI), the acylated derivative as the activated form of formula (IV) includes an acid chloride, an acid anhydride, a mixed acid anhydride (preferably, an acid anhydride formed with methyl chloroformate, methylenesulfonyl chloride, p-toluenesulfonyl chloride or chlorophosphate), an activated ester (preferably, an ester formed from the reaction with N-hydroxybenzotriazole in the presence of a condensing agent such as dicyclohexylcarbodiimide), and the like. In addition, the acylation reaction can also be carried out using a free acid of formula (IV) in the presence of a condensing agent such as dicyclohexylcarbodiimide, carbonyldiimidazole, etc. In general, the acylation reaction can be conveniently carried out in the presence of an organic base such as tertiary amines (preferably, triethylamine, dimethylaniline, pyridine, etc.) or an inorganic base such as sodium hydrogen carbonate, sodium carbonate, etc. In this reaction, the suitable solvent which can be used includes halogenated hydrocarbons such as methylene chloride, chloroform, etc., tetrahydrofuran, acetonitrile, dimethylformamide, dimethylacetamide, and the like. In addition, a mixed solvent consisting of two or more selected from the above-mentioned solvents can also be used in this reaction. The solvent may also be used in the form of an aqueous solution. The acylation reaction can be practiced at the temperature of $-50°$ C. to $50°$ C. (preferably $-30°$ C. to $20°$ C.). The acylating agent of formula (IV) can be used in an equivalent weight or a slightly excessive amount (1.05 to 1.2 equivalent weight) with respect to the compound of formula (V).

The compound of formula (II) is prepared from the compound of formula (VI), as prepared above, according to the general method. Specifically, the compound of formula (II) can be preapred by subjecting the compound of formula (VI) to a conventional method [for example, Wittig reaction] to obtain an intermediate ylide compound of formula (VII) which is then reacted with a halogenated acetaldehyde:

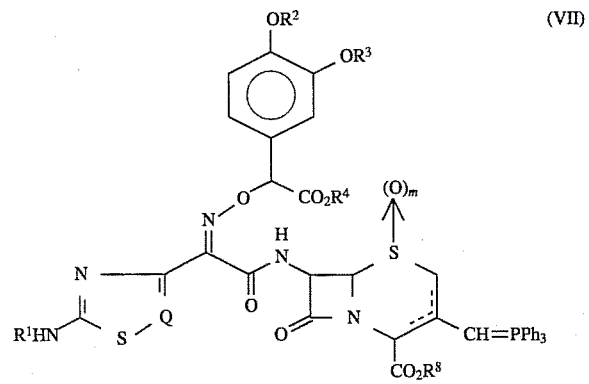

in which $R^1$ to $R^4$, Q, m and $R^8$ are defined as previously described.

Alternatively, the compound of formula (II) can also be prepared by activating the compound of formula (IV) or its salt with an acylating agent and then reacting the activated compound directly with a compound of formula (VIII):

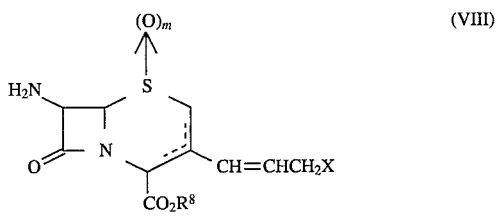

in which m, X and $R^8$ are defined as previously described.

In this method, the activation and acylation of the compound of formula (IV) are practiced according to the method as previously described.

In addition, the conversion of a halogen atom for X in the compound of formula (II) into other halogen atom can be practiced according to a conventional method. For example, the compound of formula (II) wherein X is iodine atom can be obtained by reacting the compound of formula (II) wherein X is chlorine atom with an alkali metal iodide.

In preparing the compound of formula (I), the amino-protecting group or the carboxyl-protecting group of the compound of formula (II) can be removed by a conventional method which has been well-known widely in cephalosporin field. Specifically, the protecting groups can be removed by hydrolysis or reduction. When the proecting groups contain an amido group, it is preferable to remove them by amino-halogenation or amino-etherification followed by hydrolysis. Acid hydrolysis is useful for removing tri(di)phenylmethyl or alkoxycarbonyl group and can be practiced by using an organic acid such as formic acid, trifluoroacetic acid, p-toluenesulfonic acid, etc., or an inorganic acid such as hydrochloric acid, etc.

The method for preparing the compound of formula (III) which is used in the process according to the present invention is specifically described in the following preparation examples.

Meanwhile, in preparing the compound of formula (I) by substitution of the C-3 position of the compound of formula (II) with the compound of formula (III), an organic solvent which can be used includes lower alkylnitriles such as acetonitrile, propionitrile, etc., halogenated lower alkanes such as chloromethane, dichloromethane, chloroform, etc., ethers such as tetrahydrofuran, dioxane, ethylether, etc., amides such as dimethylformamide, etc., esters such as ethylacetate, etc., ketones such as acetone, etc., hydrocarbons such as benzene, etc., alcohols such as methanol, ethanol, etc., sulfoxides such as dimethylsulfoxide, etc., and the like, or a mixture of two or more selected therefrom. The reaction can be conveniently carried out at the temperature of −10° C. to 80° C. (preferably of 20° C. to 40° C.). The compound of formula (III) can be used in an amount of 0.5 to 2 equivalent weights, preferably 1.0 to 1.1 equivalent weights, with respect to the compound of formula (II).

The reaction product produced by the above reaction can be treated with various methods such as recrystallization, ionophoresis, silica gel column chromatography, ion-exchange resin chromatography and the like, to isolate and purify the desired compound of formula (I).

As described above, the compound of formula (I) shows a broad antibacterial spectrum and more potent antimicrobial activity against various pathogenic organisms including gram-positive and gram-negative strains. Such antimicrobial activity can also be applied to numerous gram-negative bacterial strains which produce β-lactamase. Accordingly, the compound of formula (I) can be effectively used for prophylaxis and treatment of bacterial infection in animals including human being.

The compound of formula (I) according to the present invention can be formulated according to the known method using known pharmaceutical carriers and excipients into a single dosage unit or to fill into a multiple-dose container. The formulation may be in the form of a solution, suspension or emulsion in oil or aqueous medium and can contain conventional dispersants, suspending agents or stabilizers. In addition, the formulation may be prepared in the form of a dry powder which can be dissolved in a pyrogen-free, sterilized water before use. The compound of formula (I) can also be formulated into a suppository using conventional suppository bases such as coccoa butter or other glycerides. If necessary, the compound of the present invention can be administered in a combination with other antibacterial agent such as penicillins or cephalosporins.

When the compound of the present invention is formulated into a single dosage unit, it is preferable that the single dosage unit contains about 50 to 1500 mg of the compound of formula (I) as an active ingredient. The dose of the compound of formula (I) to be administered should be determined by a specialist depending on various factors such as weight and age of individual patient and the condition and severity of disease. However, the daily dosage for adult patient is generally in the range of about 500 to 5000 mg depending on the administration frequency and route. When the compound of formula (I) is administered in intramuscular or intravenous injection, a total daily dosage of about 150 to 3000 mg is sufficient for adult patient. However, in the case of infections caused by some bacterial strains a more increased daily dosage may be preferable.

The compound of formula (I) and its non-toxic salts (preferably alkali metal salt, alkaline earth metal salt, inorganic acid addition salt, organic acid addition salt and salt with amino acid) according to the present invention are very useful for prophylaxis and treatment of diseases caused by bacterial infections in animals including human being, due to their potent antimicrobial activity against various pathogenic microorganisms including gram-positive and gram-negative bacterial strains.

Typical examples of the compound of formula (I) according to the present invention are listed in the following.

TYPICAL COMPOUNDS

I-1: 7-[(Z)-2-(2-aminothiazol-4-yl)-2-(α-carboxy-3,4-dihydroxybenzyloxyimino)acetamido]-3-[(E)-3-(4,6-diaminopyrimidinium- 1-yl)-1-propen-1-yl]-3-cephem-4-carboxylate

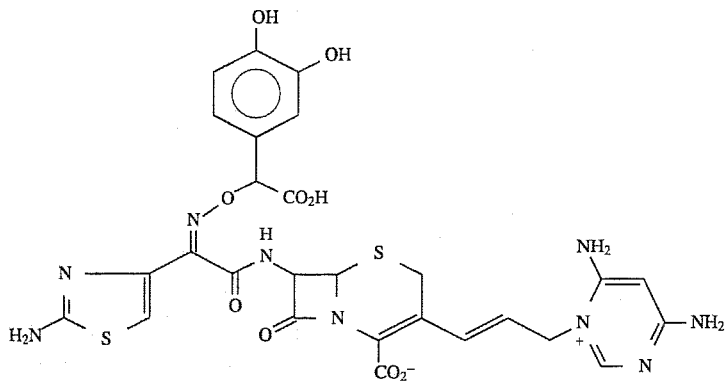

I-2: 7-[(Z)-2-(2-aminothiazol-4-yl)-2-(α-carboxy-3,4-dihydroxybenzyloxyimino)acetamido]-3-[(E)-3-(4-aminopyrimidinium-1-yl)-1-propen-1-yl]-3-cephem-4-carboxylate

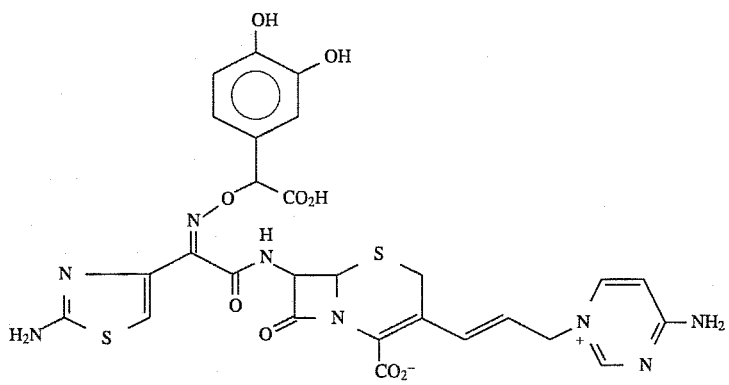

I-3: 7-[(Z)-2-(2-aminothiazol-4-yl)-2-(α-carboxy-3,4-dihydroxybenzyloxyimino)acetamido]-3-[(E)-3-(4-amino-5,6-cyclopentanopyrimidinium-1-yl)-1-propen-1-yl]-3-cephem-4-carboxylate

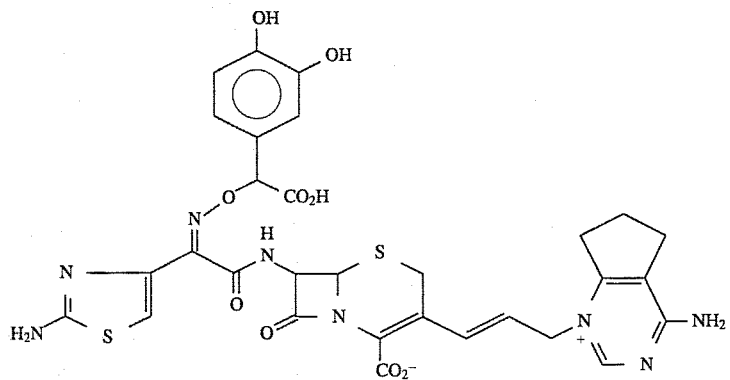

I-4: 7-[(Z)-2-(2-aminothiazol-4-yl)-2-(α-carboxy-3,4-dihydroxybenzyloxyimino)acetamido]-3-[(E)-3-(4,6-diamino-5-methylpyrimidinium-1-yl)-1-propen-1-yl]-3-cephem-4-carboxylate

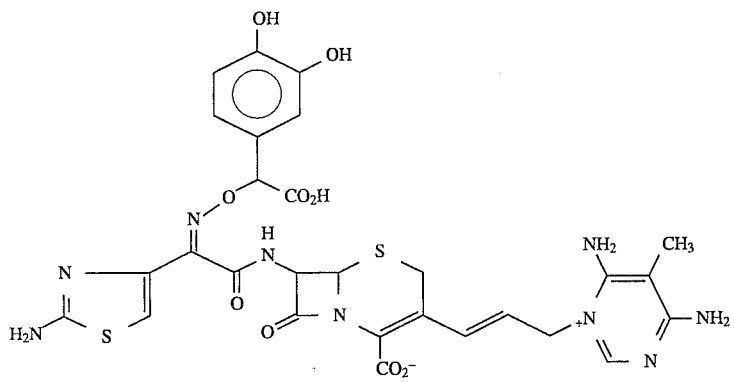

(I-4)

I-5: 7-[(Z)-2-(2-aminothiazol-4-yl)-2-(α-carboxy-3,4-dihydroxybenzyloxyimino)acetamido]-3-[(E)-3-(4,5,6-triaminopyrimidinium- 1-yl)-1-propen-1-yl]-3-cephem-4-carboxylate NMR (δ, acetone-$d_6$): 5.2(d, 1H), 6.0(d, 1H), 6.8(d, 1H), 7.0(d, 1H), 7.2(d, 1H), 7.9(s, 1H), 8.0(s, 1H)

B. Synthesis of α-trichloromethyl-3,4-O-isopropylidenedioxybenzyl alcohol

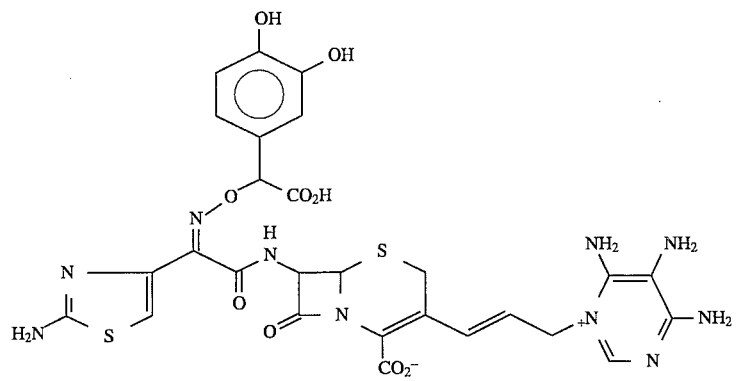

(I-5)

Hereinafter, the present invention will be more specifically explained on the basis of the following preparation examples and working examples. However, it should be understood that the present invention is not limited by these examples in any manner.

PREPARATION 1

Synthesis of 2-bromo-2-(3,4-O-isopropylidenedioxyphenyl)acetic acid diphenylmethyl ester A. Synthesis of 2-(3,4-dihydroxyphenyl)-2-hydroxy-1,1,1-trichloroethane To the solution of 440 g of 1,2-dihydroxybenzene dissolved in 1 L of methylene dichloride was added 1036 g of trichloroacetaldehyde monohydrate and then the reaction solution was cooled down to 0° C. 102 g of triethylamine was slowly added dropwise thereto. The reaction solution was warmed to room temperature, stirred for about 20 minutes, heated to 50° C. and then stirred for further 3 hours while maintaining the same temperature. After the reaction is completed, the reaction mixture was distilled under reduced pressure to remove methylene dichloride. The residue was dissolved in 4 L of ethylacetate, washed successively with 2400 ml of 0.5N-aqueous hydrochloric acid solution and 2 L of saturated saline, dried over anhydrous magnesium sulfate and then distilled under reduced pressure to remove the solvent and to obtain 540 g of the title compound.

515 g of 2-(3,4-dihydroxyphenyl)-2-hydroxy-1,1,1-trichloroethane synthesized in Preparation 1(A) was dissolved in 2.5 L of benzene and then 305 ml of 2,2-dimethoxypropane and 2.84 g of phosphorus pentoxide were added thereto. The reaction mixture was then heated under reflux. This reaction was carried out in a reaction vessel equipped with Soxhlet extractor wherein the extracting tube was filled with 600 g of calcium chloride to remove the reaction by-product, methanol. After 2 hours, 77 ml of 2,2-dimethoxypropane was added to the reaction mixture and the mixture was heated under reflux for further 3 hours. After the reaction is completed, the reaction solution was cooled to room temperature, washed successively with 1N-aqueous sodium hydrogen carbonate solution (500 ml×4) and saturated saline (500 ml×4), dried over anhydrous magnesium sulfate and then distilled under reduced pressure to remove the solvent. The residue was purified by silica gel column chromatography to obtain 220 g of the oily title compound.

NMR (δ, $CDCl_3$): 1.66(s, 6H), 3.61(d, 1H), 4.98(d, 1H), 6.53–6.90(m, 3H)

C. Synthesis of 2-(3,4-O-isopropylidenedioxyphenyl)-2-hydroxyacetic acid 119.4 g of lithium hydroxide monohydrate was dissolved in 500 ml of water and then cooled down to 0° C. To the resulting solution were added 201 g of α-trichloromethyl-3,4-O-isopropylidene-dioxybenzyl alcohol prepared in Preparation 1(B) and 413 ml of dioxane and the mixture was stirred at room temperature for 3 days. After the reaction is completed, to the reaction solution was added 240 g of ice and then 300 ml of 6N-aqueous hydrochloric acid solution and 120 g of ice were added thereto. The mixture was stirred for 30 minutes to precipitate the solid product which was then filtered, washed with 1.8 L of water and 700 ml of chloroform and dried under $N_2$ to obtain 60 g of the title compound.

NMR (δ, DMSO-$d_6$): 1.61(s, 6H), 4.85(s, 1H), 6.60–6.83(m, 3H), 8.2(bs, 2H)

D. Synthesis of 2-(3,4-O-isopropylidenedioxyphenyl)-2-hydroxyacetic acid diphenylmethyl ester 50 g of 2-(3,4-O-isopropylidenedioxyphenyl)-2-hydroxyacetic acid prepared in Preparation 1(C) was dissolved in 400 ml of acetone and then 1M diphenyldiazomethane dissolved in diethylether was added dropwise thereto until nitrogen gas is no more generated. After the addition is completed, the reaction mixture was stirred for further 20 minutes and then distilled under reduced pressure to remove the solvent. The residue was purified by silica gel column chromatography to obtain 70 g of the title compound.

NMR (δ, $CDCl_3$): 1.69(s, 6H), 5.62(d, 1H), 6.20(d, 1H), 6.70(d, 1H), 6.87(s, 1H), 6.89(d, 1H), 6.97(s, 1H), 7.26(b, 10H)

E. Synthesis of 2-bromo-2-(3,4-O-isopropylidenedioxyphenyl)acetic acid diphenylmethyl ester 108 g of 2-(3,4-O-isopropylidenedioxyphenyl)-2-hydroxyacetic acid diphenylmethyl ester prepared in Preparation 1(D) was dissolved in 1.3 L of dimethylformamide and then the reaction solution was cooled down to −60° C. 187.4 g of phosphorus tribromide was added thereto and then the temperature of the reaction solution was increased to −15° C. The reaction mixture was stirred for 20 minutes. After the reaction is completed, the reaction solution was distilled under reduced pressure to remove the solvent. The residue was dissolved in 1 L of ethylacetate, washed with saturated saline (1 L×4), dried over anhydrous magnesium sulfate and then distilled under reduced pressure to remove the solvent and to obtain 115.96 g of the title compound.

NMR (δ, $CDCl_3$): 1.66(d, 6H), 5.41(s, 1H), 6.63(d, 1H), 6.84(s, 1H), 6.86(d, 1H), 6.97(s, 1H), 7.25(b, 10H)

PREPARATION 2

Synthesis of 2-{2-(triphenylmethyl)aminothiazol-4-yl}-2-(α-diphenylmethyloxycarbonyl-3,4-O-isopropylidenedioxybenzyloxyimino)acetic acid A. Synthesis of 2-{2-(triphenylmethyl)aminothiazol-4-yl}-2-(α-diphenylmethyloxycarbonyl- 3,4-O-isopropylidenedioxybenzyloxyimino)acetic acid allyl ester To the solution of 58.18 g of 2-(2-triphenylmethylaminothiazol- 4-yl)-2-hydroxyiminoacetic acid allyl ester dissolved in 140 ml of dimethylformamide were added 61 g of potassium carbonate and 29.4 g of potassium iodide. The reaction solution was cooled down to 0° C. and then the solution of 80.16 g of 2-bromo-2-(3,4-O-isopropylidenedioxyphenyl)acetic acid diphenylmethyl ester prepared in Preparation 1(E) which is dissolved in 60 ml of dimethylformamide was added dropwise thereto over one hour. The reaction mixture was then stirred for further 20 minutes. After the reaction is completed, the reaction solution was distilled under reduced pressure to remove the solvent. The residue was dissolved in 2 L of ethylacetate, washed with saturated saline (400 ml×6), dried over anhydrous magnesium sulfate and then distilled under reduced pressure to remove the solvent. The resulting solid was purified by silica gel column chromatography to obtain 89 g of the title compound.

NMR (δ, $CDCl_3$): 1.69(s, 6H), 4.81(d, 2H), 5.27(ABq, 2H), 5.79(s, 1H), 5.80–5.99(m, 1H), 6.53(s, 1H), 6.64(d, 1H), 6.78(d, 1H), 6.87(s, 1H), 7.13–7.36(m, 27H)

B. Synthesis of 2-{2-(triphenylmethyl)aminothiazol-4-yl}-2-(α-diphenylmethyloxycarbonyl- 3,4-O-isopropylidenedioxybenzyloxyimino)acetic acid 60 g of 2-{2-(triphenylmethyl)aminothiazol-4-yl}-2-(α-diphenylmethyloxycarbonyl- 3,4-O-isopropylidenedioxybenzyloxyimino)acetic acid allyl ester prepared in Preparation 2(A) was dissolved in 500 ml of methylene dichloride. To the resulting solution were added 14.5 g of potassium 2-ethylhexanoate, 3.75 g of triphenylphosphine and 0.6 g of tetrakis(triphenylphosphine)palladium and the mixture was stirred at room temperature for one hour. After the reaction is completed, the reaction solution was washed with saturated saline (500 ml×3), dried over anhydrous magnesium sulfate and then distilled under reduced pressure to remove the solvent. The residue was purified by silica gel column chromatography to obtain 50 g of the title compound.

NMR (δ, $CDCl_3$): 1.70(s, 6H), 5.68(s, 1H), 6.55(s, 1H), 6.66(d, 1H), 6.80(d, 1H), 6.89(s, 1H), 7.04–7.27(m, 27H)

PREPARATION 3

Synthesis of paramethoxybenzyl 3-chloromethyl-7-[(Z)-2-(α-diphenylmethyloxycarbonyl-3,4-O-isopropylidenedioxybenzyloxyimino)-2-{2-(triphenylmethyl)aminothiazol-4-yl}acetamido]-3-cephem-4-carboxylate 36 g of paramethoxybenzyl 7-amino-3-chloromethyl-3-cephem-4-carboxylate was suspended in 950 ml of methylene dichloride and 28.1 g of pyridine was added thereto. The reaction solution was cooled to −20° C. and 50.09 g of 2-{2-(triphenylmethyl)aminothiazol- 4-yl}-2-(α-diphenylmethyloxycarbonyl-3,4-O-isopropylidenedioxybenzyloxyimino)acetic acid prepared in Preparation 2(B) was added thereto. The reaction mixture was stirred for 5 minutes, and 13.62 g of phosphorus oxychloride was added thereto and then the mixture was stirred for further 30 minutes. After the reaction is completed, the reaction solution was washed with saturated saline (400 ml×3), dried over anhydrous magnesium sulfate and then distilled ubder reduced pressure to remove the solvent. The resulting solid was purified by silica gel column chromatography to obtain 70 g of the title compound as a foamy solid.

NMR (δ, $CDCl_3$): 1.59(d, 6H), 3.33(ABq, 2H), 3.83(s, 3H), 4.51(ABq, 2H), 4.96(d, 1H), 6.27(s, 2H), 5.87(dd, 1H), 5.95(s, 1H), 6.6–7.45(m, 35H), 8.21(d, 1H)

PREPARATION 4

Synthesis of paramethoxybenzyl 7-[(Z)-2-(α-diphenylmethyloxycarbonyl-3,4-O-isopropylidenedioxybenzyloxyimino)-2-{2-(triphenylmethyl)aminothiazol-4-yl}acetamido]-3-[(Z)-3-chloro-1-propen-1-yl]-3-cephem-4-carboxylate A. Synthesis of paramethoxybenzyl 7-[(Z)-2-(α-diphenylmethyloxycarbonyl- 3,4-O-isopropylidenedioxybenzyloxyimino)-2-{2-(triphenylmethyl)aminothiazol-4-yl}acetamido]-3-triphenylphosphoniummethyl-3-cephem-4-carboxylate iodide 28.41 g of the compound prepared in Preparation 3 was dissolved in 150 ml of acetone and then 7.52 g of triphenylphosphine and 3.76 g of sodium iodide were successively added thereto. The reaction mixture was stirred at room temperature for 40 minutes. After the reaction is completed, the reaction solution was distilled under reduced pressure to remove the solvent. To the residue were added 300 ml of dichloromethane and 300 ml of distilled water, and the mixture was thoroughly shaked to separate the layers. The separated organic layer was dried over 50 g of anhydrous magnesium sulfate and then distilled under reduced pressure to remove the solvent. The resulting solid product was washed with 400 ml of diethylether and then dried to obtain 32.3 g of the title compound as a pale yellow powder.

NMR (δ, CDCl$_3$): 1.58(d, 6H), 3.34(ABq, 2H), 3.85(s, 3H), 3.88(ABq, 2H), 4.98(d, 1H), 5.30(s, 2H), 5.74–5.92(m, 2H), 5.96(s, 1H), 6.57(d, 1H), 6.63–7.42(m, 35H), 8.26(d, 1H)

B. Synthesis of paramethoxybenzyl 7-[(Z)-2-(α-diphenylmethyloxycarbonyl- 3,4-O-isopropylidenedioxybenzyloxyimino)-2-{2-(triphenylmethyl)aminothiazol-4-yl}acetamido]-3-[(Z)-3-chloro-1-propen- 1-yl]-3-cephem-4-carboxylate 32.3 g of the compound prepared in Preparation 4(A) was dissolved in the mixed solvent of 300 ml of chloroform and 100 ml of aqueous saturated sodium chloride solution and then 28 ml of 1N-aqueous sodium hydroxide solution was added thereto. The reaction mixture was stirred at 15° C. for 20 minutes. After the reaction is completed, the reaction solution was allowed to stand to separate the layers. To the separated organic layer was added 10 g of potassium carbonate and the mixture was stirred for 10 minutes and then filtered. 18.06 g of 40% aqueous chloroacetaldehyde solution was added to the filtrate and the mixture was stirred at 28° C. for 30 minutes. After the reaction is completed, the reaction solution was allowed to separate the layers and the separated organic layers were dried over anhydrous magnesium sulfate and then distilled under reduced pressure to remove the solvent. The resulting solid product was purified by silica gel column chromatography to obtain 17.24 g of the title compound as a white powder.

NMR (δ, CDCl$_3$): 1.60(d, 6H), 3.32(ABq, 2H), 3.82(s, 3H), 3.84(ABq, 2H), 4.96(d, 1H), 5.28(s, 2H), 5.76–5.84(m, 2H), 5.95(s, 1H), 6.53(d, 1H), 6.63–7.45(m, 35H), 8.21(d, 1H)

PREPARATION 5

Synthesis of paramethoxybenzyl 7-[(Z)-2-(α-diphenylmethyloxycarbonyl-3,4-O-isopropylidenedioxybenzyloxyimino)-2-{2-(triphenylmethyl)aminothiazol-4-yl}acetamido]-3-[(Z)-3-iodo-1-propen-1-yl]-3-cephem- 4-carboxylate 17.24 g of the compound prepared in Preparation 4(B) was dissolved in 200 ml of acetone and then 11.32 g of sodium iodide was added thereto. The reaction mixture was stirred at 15° C. to 20° C. for 2 hours. After the reaction is completed, the reaction solution was distilled under reduced pressure to remove the solvent. The residue was extracted with 300 ml of ethylacetate, washed three times with 300 ml of saturated saline, dried over anhydrous sodium sulfate, distilled under reduced pressure to remove the solvent and then concentrated. The residue was slowly added dropwise to 300 ml of diethylether to solidify the resulting product which was then filtered, washed with 200 ml of diethylether and dried to obtain 15.3 g of the title compound as a pale yellow solid.

NMR (δ, CDCl$_3$): 1.60(d, 6H), 3.34(ABq, 2H), 3.81(s, 3H), 3.83(ABq, 2H), 4.98(d, 1H), 5.26(s, 2H), 5.76–5.83(m, 2H), 5.97(s, 1H), 6.53(d, 1H), 6.65–7.43(m, 35H), 8.23(d, 1H)

PREPARATION 6

Synthesis of 4,6-diaminopyrimidine 167.78 g of 2-mercapto-4,6-diaminopyrimidine was dissolved in 1007 ml of 1.5N-aqueous sodium hydroxide solution, and the reaction solution was cooled down to 0° to 4° C. To this reaction solution was slowly added dropwise 267.55 g of 30% aqueous hydrogen peroxide solution. After the addition is completed, 170 ml of acetic acid was slowly added dropwise to the reaction solution to precipitate the solid product which was then filtered, washed successively with 200 ml of distilled water, 200 ml of methanol and 400 ml of diethylether and dried to obtain 185.56 g of the solid product as a white powder. The solid product thus obtained was slowly added to 1 L concentrated hydrochloric acid which was cooled to 0° C. to 4° C. The reaction solution was stirred for one hour at the same temperature, warmed to room temperature and then stirred for further 8 hours. The solid product produced during the reaction was filtered, washed with 1 L of acetone and 1 L of diethylether and then dried to obtain 109.13 g of the title compound in the form of hydrochloride salt. 109.13 g of the solid thus obtained was suspended in 400 ml of distilled water, and 200 ml of 15% aqueous sodium hydroxide solution was then added thereto. The mixture was stirred at room temperature for one hour and filtered. The filtered solid product was washed with 400 ml of ethanol and then dried to obtain 100.7 g of the title compound as a white powder.

NMR (δ, DMSO-d$_6$): 5.34(s, 1H), 6.01(s, 4H), 7.78(s, 1H)

PREPARATION 7

Synthesis of 4-aminopyrimidine

According to the same procedure as Preparation 6 except that 150.07 g of 2-mercapto-4-aminopyrimidine is used instead of 167.78 g of 2-mercapto-4,6-diaminopyrimidine used in Preparation 6, 91.24 g of the title compound was obtained as a white powder.

NMR (δ, DMSO-d$_6$): 6.42(d, 1H), 6.85(s, 2H), 8.04(d, 1H), 8.36(s, 1H)

PREPARATION 8

Synthesis of 5-methyl-4,6-diaminopyrimidine

According to the same procedure as Preparation 6 except that 184.30 g of 2-mercapto-5-methyl-4,6-diaminopyrimidine is used instead of 2-mercapto-4,6-diaminopyrimidine used in Preparation 6, 109.47 g of the title compound was obtained as a white powder.

NMR (δ, DMSO-d$_6$): 1.83(s, 3H), 6.48(s, 4H), 7.84(s, 1H)

PREPARATION 9

Synthesis of 4-amino-5,6-cyclopentapyrimidine

According to the same procedure as Preparation 6 except that 210.25 g of 2-mercapto-4-amino-5,6-cyclopentapyrimidine is used instead of 2-mercapto-4,6-diaminopyrimidine used in Preparation 6, 124.32 g of the title compound was obtained as a white powder.

NMR (δ, DMSO-$d_6$): 1.96(m, 2H), 2.62(t, 2H), 2.68(t, 2H), 6.56(s, 2H), 8.13(s, 1H)

PREPARATION 10

Synthesis of 4,5,6-triaminopyrimidine

According to the same procedure as Preparation 6 except that 200 g of 2-mercapto-4,5,6-triaminopyrimidine is used instead of 2-mercapto- 4,6-diaminopyrimidine used in Preparation 6, 89 g of the title compound was obtained as a white powder.

NMR (δ, DMSO-$d_6$): 3.82(s, 2H), 5.60(s, 4H), 7.42(s, 1H)

Hereinafter, each compound of Examples 1 to 5 can be present as two diastereoisomers (R and S isomer) depending on the steric configuration of the asymmetric carbon atom to which 7β dihydroxybenzyl group is attached. In addition, when the compound is subjected to high pressure liquid chromatography(HPLC) using μ-Bondapak $C_{18}$ Steel column eluting with 25% aqueous methanol solution containing 0.5% acetic acid, the compounds having a short retention time and a long retention time were distinguished from each other by appending 'a' and 'b', respectively, to the number of individual compound.

EXAMPLE 1

Synthesis of
7-[(Z)-2-(2-aminothiazol-4-yl)-2-(α-carboxy-
3,4-dihydroxybenzyloxyimino)acetamido]-3-[(E)-3-
(4,6-diaminopyrimidinium-1-yl)-
1-propen-1-yl]-3-cephem- 4-carboxylate (S-form:
I-1a, R-form: I-1b)

5.0 g of the compound prepared in Preparation 5 was dissolved in 20 ml of dimethylformamide and 1.52 g of 4,6-diaminopyrimidine prepared in Preparation 6 was added thereto. The reaction mixture was stirred at 35° to 40° C. for 2 hours. After the reaction is completed, the reaction solution was extracted with 200 ml of ethylacetate. The extract was washed three times with 200 ml of saturated saline, dried over anhydrous magnesium sulfate and then distilled under reduced pressure to remove the solvent. The concentrate thus obtained was slowly added dropwise to 300 ml of diethylether to precipitate the solid product which was filtered, washed with 200 ml of diethylether and then dried to obtain 4.3 g of the solid product as a white powder. 4.3 g of the obtained solid product was dissolved in 13 ml of anisole. The reaction solution was cooled down to 0° C. to 4° C. After slowly adding dropwise 26 ml of trifluoroacetic acid thereto, the reaction solution was warmed to room temperature and then stirred for further one hour at the same temperature. After the reaction is completed, the reaction solution was cooled down to −10° C. to −15° C. To this reaction solution was slowly added dropwise 150 ml of diethylether to precipitate the solid product which was then filtered, washed successively with 100 ml of acetone and 100 ml of diethylether and dried to obtain 1.8 g of the pale yellow solid. 1.8 g of the solid thus obtained was separated as respective diastereoisomer by fractional liquid chromatography (μ-Bondapak $C_{18}$ Steel Column, 19 mm×30 mm) eluting with 5% aqueous methanol solution to obtain 320 mg and 280 mg of the title compounds I-1a and I-1b, respectively, as a white solid.

M.S. (FAB, M+1): 684

NMR (δ, $D_2O$+$NaHCO_3$)

I-1a: 3.33(ABq, 2H), 4.71(ABq, 2H), 5.02(d, 1H), 5.37(s, 1H), 5.63(d, 1H), 5.77(s, 1H), 5.72–5.95 (m, 1H), 6.55(d, 1H), 6.77–7.02(m, 4H), 8.16(s, 1H)

I-1b: 3.33(ABq, 2H), 4.78(ABq, 2H), 5.01(d, 1H), 5.38(s, 1H), 5.61(d, 1H), 5.79(s, 1H), 5.82–5.96 (m, 1H), 6.58(d, 1H), 6.76–7.01(m, 4H), 8.17(s, 1H)

IR (KBr, $cm^{-1}$): 1775(β-lactam), 1670, 1620, 1580

EXAMPLE 2

Synthesis of
7-[(Z)-2-(2-aminothiazol-4-yl)-2-(α-carboxy-
3,4-dihydroxybenzyloxyimino)acetamido]-3-[(E)-3-(4
-aminopyrimidinium-1-yl)-1-
propen-1-yl]-3-cephem-4-carboxylate (S-form: I-2a,
R-form: I-2b)

5.0 g of the compound prepared in Preparation 5 was dissolved in 20 ml of dimethylformamide and then the reaction solution was treated according to the same procedure as Example 1, except that 1.36 g of 4-aminopyrimidine prepared in Preparation 7 is used instead of 4,6-diaminopyrimidine used in Example 1, to obtain 360 mg and 340 mg of the title compounds I-2a and I-2b, respectively, as a white solid.

M.S. (FAB, M+1): 669

NMR (δ, $D_2O$+$NaHCO_3$)

I-2a : 3.37(ABq, 2H), 4.73(ABq, 2H), 5.02(d, 1H), 5.37(s, 1H), 5.66(d, 1H), 5.82–5.96(m, 1H), 6.70–7.01(m, 6H), 7.98(d, 1H), 8.53(s, 1H)

I-2b : 3.33(ABq, 2H), 4.78(ABq, 2H), 5.01(d, 1H), 5.38(s, 1H), 5.61(d, 1H), 5.82–5.96(m, 1H), 6.70–7.01(m, 6H), 7.98(d, 1H), 8.53(s, 1H)

IR (KBr, $cm^{-1}$): 1775 (β-lactam), 1680, 1630, 1590

EXAMPLE 3

Synthesis of
7-[(Z)-2-(2-aminothiazol-4-yl)-2-(α-carboxy-
3,4-dihydroxybenzyloxyimino)acetamido]-3-
[(E)-3-(4-amino-5,6-
cyclopentanopyrimidinium-1-yl)-
1-propen-1-yl]-3-cephem-4-carboxylate (S-form:
I-3a, R-form: I-3b)

5.0 g of the compound prepared in Preparation 5 was dissolved in 20 ml of dimethylformamide and then the reaction solution was treated according to the same procedure as Example 1, except that 1.90 g of 4-amino-5,6-cyclopentanopyrimidine prepared in Preparation 9 is used instead of 4,6-diaminopyrimidine used in Example 1, to obtain 290 mg and 285 mg of the title compounds I-3a and I-3b, respectively, as a white solid.

M.S. (FAB, M+1): 697

NMR (δ, $D_2O$+$NaHCO_3$)

I-3a: 2.11–2.31(m, 2H), 2.79(t, 2H), 3.08(t, 2H), 3.35(ABq, 2H), 4.73(ABq, 2H), 5.03(d, 1H), 5.38(s, 1H), 5.66(d, 1H), 5.84–6.01(m, 1H), 6.56(d, 1H), 6.77–7.01(m, 4H), 8.44(s, 1H)

I-3b : 2.12–2.29(m, 2H), 2.79(t, 2H), 3.06(t, 2H), 3.34(ABq, 2H), 4.72(ABq, 2H), 5.02(d, 1H), 5.38(s, 1H), 5.64(d, 1H), 5.82–6.01(m, 1H), 6.58(d, 1H), 6.77–7.02(m, 4H), 8.43(s, 1H)

IR (KBr, cm$^{-1}$) : 1770($\beta$-lactam), 1670, 1640, 1580

EXAMPLE 4

Synthesis of
7-[(Z)-2-(2-aminothiazol-4-yl)-2-($\alpha$-carboxy-3,4-dihydroxybenzyloxyimino)acetamido]-3-[(E)-3-(4,6-diamino-5-methylpyrimidinium-1-yl)-1-propen-1-yl]-3-cephem-4-carboxylate (S-form: I-4a, R-form: I-4b)

5.0 g of the compound prepared in Preparation 5 was dissolved in 20 ml of dimethylformamide and then the reaction solution was treated according to the same procedure as Example 1, except that 1.67 g of 4,6-diamino-5-methylpyrimidine prepared in Preparation 8 is used instead of 4,6-diaminopyrimidine used in Example 1, to obtain 300 mg and 305 mg of the title compounds I-4a and I-4b, respectively, as a white solid.

M.S. (FAB, M+1): 698

NMR ($\delta$, D$_2$O+NaHCO$_3$)

I-4a: 1.85(s, 3H), 3.34(ABq, 2H), 4.76(ABq, 2H), 5.00(d, 1H), 5.38(s, 1H), 5.62(d, 1H), 5.68–5.92 (m, 1H), 6.63(d, 1H), 6.80–7.01(m, 4H), 8.18(s, 1H)

I-4b: 1.84(s, 3H), 3.34(ABq, 2H), 4.73(ABq, 2H), 5.00(d, 1H), 5.38(s, 1H), 5.62(d, 1H), 5.68–5.92 (m, 1H), 6.63(d, 1H), 6.80–7.01(m, 4H), 8.17(s, 1H)

IR (KBr, cm$^{-1}$): 1770($\beta$-lactam), 1680, 1620, 1570

EXAMPLE 5

Synthesis of
7-[(Z)-2-(2-aminothiazol-4-yl)-2-($\alpha$-carboxy-3,4-dihydroxybenzyloxyimino)acetamido]-3-[(E)-3-(4,5,6-triaminopyrimidinium-1-yl)-1-propen-1-yl]-3-cephem-4-carboxylate (S-form: I-5a, R-form: I-5b)

5.0 g of the compound prepared in Preparation 5 was dissolved in 20 ml of dimethylformamide and then the reaction solution was treated according to the same procedure as Example 1, except that 1.9 g of 4,5,6-triaminopyrimidine prepared in Preparation 10 is used instead of 4,6-diaminopyrimidine used in Example 1, to obtain 330 mg and 340 mg of the title compounds I-5a and I-5b, respectively, as a white solid.

M.S. (FAB, M+1) : 699

NMR ($\delta$, D$_2$O+NaHCO$_3$)

I-5a: 3.32(ABq, 2H), 4.70(ABq, 2H), 5.04(d, 1H), 5.32(s, 1H), 5.64(d, 1H), 5.70–5.91(m, 1H), 6.57(d, 1H), 6.71–7.05(m, 4H), 7.49(s, 1H)

I-5b: 3.32(ABq, 2H), 4.74(ABq, 2H), 5.03(d, 1H), 5.33(s, 1H), 5.61(d, 1H), 5.77–5.93(m, 1H), 6.58(d, 1H), 6.70–7.04(m, 4H), 7.50(s, 1H)

IR (KBr, cm$^{-1}$) : 1770($\beta$-lactam), 1680, 1610, 1580

The pharmacological utility of the compound according to the present invention was estimated from the minimum inhibitory concentration against test strains including standard strains, strains isolated in the clinical field, strains resistant to some antibiotics and $\beta$-lactamase producing strains and the pharmacokinetic properties in rats, as compared with Ceftazidime as the control medicine. The minimum inhibitory concentration was determined by diluting the test compounds according to 2-fold dilution, suspending them in Müller-Hinton agar medium, inoculating 2 $\mu$l of the suspension containing the test strains having 10$^7$ CFU (Colony Forming Unit) per 1 ml into the medium and then culturing the test strains at 37° C. for 20 hours. The results are described in the following Table 1.

The pharmacokinetic properties of the compound of the present invention were determined using SD rats ($\delta$) weighing 230±10 g. Specifically, the test samples were injected into femoral vein in an amount of 20 mg/kg to 4 to 5 test animals. Blood was taken from femoral vein 1, 2.5, 5, 10, 20, 40, 60, 120 and 180 minutes after administration and then subjected to a biological assay using agar well method to measure the blood concentration. The results of pharmacokinetic properties, i.e. T½ and AUC (Area Under the Curve), calculated from the above blood concentration are described in the following Table 2.

TABLE 1

| | Minimum Inhibitory Concentration ($\mu$g/ml) against test strains | | | | | | | | | | |
|---|---|---|---|---|---|---|---|---|---|---|---|
| | Compound | | | | | | | | | | |
| Test strains | I-1a | I-1b | I-2a | I-2b | I-3a | I-3b | I-4a | I-4b | I-5a | I-5b | CAZ* |
| Staphylococcus aureus 6538P | 0.5 | 0.5 | 0.5 | 0.5 | 1 | 0.5 | 0.5 | 0.5 | 0.5 | 0.5 | 16 |
| Staphylococcus aureus giorgio | 0.5 | 0.5 | 0.25 | 0.25 | 1 | 0.5 | 0.25 | 0.5 | 0.25 | 0.5 | 4 |
| Staphylococcus aureus 77 | 4 | 2 | 4 | 2 | 4 | 4 | 2 | 2 | 2 | 2 | 32 |
| Staphylococcus aureus 241 | 64 | 128 | 128 | 128 | >128 | >128 | 64 | 128 | 128 | 128 | >128 |
| Staphylococcus aureus epidermidis 887E | 64 | 64 | 32 | 8 | 64 | 64 | 16 | 32 | 64 | 64 | >128 |
| Streptococcus faecalis 29212A | 4 | 8 | 4 | 4 | 4 | 8 | 4 | 8 | 4 | 8 | >128 |
| Escherichia coli 10536 | ≦0.008 | 0.13 | 0.016 | 0.13 | 0.008 | 0.13 | 0.008 | 0.13 | 0.016 | 0.13 | 0.13 |
| Escherichia coli 3190Y | 0.031 | 0.13 | 0.063 | 0.13 | 0.031 | 0.25 | 0.063 | 0.13 | 0.063 | 0.13 | 0.063 |
| Escherichia coli 851E | 0.031 | 0.13 | 0.063 | 0.13 | 0.031 | 0.25 | 0.063 | 0.13 | 0.063 | 0.13 | 0.063 |
| Escherichia coli TEM1 1193E | 0.031 | 0.25 | 0.063 | 0.25 | 0.063 | 0.25 | 0.063 | 0.25 | 0.063 | 0.25 | 0.25 |

TABLE 1-continued

Minimum Inhibitory Concentration (μg/ml) against test strains

| Test strains | I-1a | I-1b | I-2a | I-2b | I-3a | I-3b | I-4a | I-4b | I-5a | I-5b | CAZ* |
|---|---|---|---|---|---|---|---|---|---|---|---|
| Escherichia coli TEM3 3455E | 0.13 | 0.5 | 0.063 | 0.25 | 0.063 | 0.5 | 0.25 | 0.5 | 0.063 | 0.063 | 8 |
| Escherichia coli TEM5 3739E | 0.5 | 2 | 0.5 | 0.1 | 0.5 | 2 | 2 | 1 | 0.5 | 1 | 8 |
| Escherichia coli TEM7 3457E | 0.13 | 0.25 | 0.031 | 0.25 | 0.13 | 0.5 | 0.25 | 0.25 | 0.031 | 0.25 | 16 |
| Escherichia coli TEM9 2639E | 2 | 2 | 1 | 0.5 | 2 | 2 | 2 | 1 | 1 | 1 | >128 |
| Pseudomonas aeruginosa 1912E | 0.5 | 64 | 0.5 | 8 | 0.5 | 8 | 4 | 8 | 0.5 | 1 | 1 |
| Pseudomonas aeruginosa 10145 | 0.25 | 32 | 0.25 | 8 | 0.5 | 8 | 0.5 | 4 | 0.25 | 2 | 2 |
| Pseudomonas aeruginosa 6065 | 1 | 32 | 4 | 64 | 1 | 64 | 1 | 16 | 4 | 8 | 16 |
| Acinetobacter calcoaceticus 15473A | 1 | 4 | 0.5 | 2 | 0.5 | 4 | 0.5 | 4 | 0.5 | 1 | 2 |
| Citrobacter diversus 2046E | 0.13 | 16 | 0.13 | 4 | 0.063 | 4 | 0.13 | 4 | 0.13 | 4 | 0.5 |
| Enterobacter cloacae IND + VE 1194E | 4 | 64 | 1 | 16 | 2 | 32 | 2 | 8 | 1 | 8 | 128 |
| Enterobacter cloacae P99 | 32 | 128 | 8 | 32 | 16 | 64 | 8 | 16 | 8 | 16 | 64 |
| Klebsiella aerogenes SHV-1 1976E | 0.13 | 1 | 0.5 | 1 | 0.13 | 1 | 0.13 | 1 | 0.5 | 1 | 0.25 |
| Klebsiella aerogenes K1 + 1082E | 0.063 | 2 | 0.13 | 2 | 0.063 | 1 | 0.063 | 2 | 0.063 | 1 | 0.5 |
| Proteus vulgaris 6059A | 0.063 | 0.5 | 0.063 | 0.5 | 0.13 | 1 | 0.063 | 1 | 0.063 | 1 | 0.063 |
| Serratia marcescens 1826E | 0.25 | 2 | 0.5 | 1 | 0.5 | 4 | 0.25 | 2 | 0.5 | 2 | 0.25 |
| Salmonella typhimurium 14028A | 0.016 | 0.13 | 0.03 | 0.25 | 0.031 | 0.13 | 0.016 | 0.13 | 0.03 | 0.031 | 0.25 |

*CAZ: Ceftazidime

TABLE 2

Pharmacokinetic properties

| Properties | I-1a | I-2a | I-3a | I-4a | I-5a | Ceftazidime |
|---|---|---|---|---|---|---|
| T ½ (min) | 34 | 55 | 33 | 53 | 41 | 20 |
| AUC (μg, min/ml) | 1964 | 3215 | 2197 | 3187 | 2977 | 1863 |

Although this invention has been described in its preferred form with a certain degree of particularity, it is appreciated by those skilled in the art that the present disclosure of the preferred form has been made only by way of example and that numerous changes in the details of the construction, combination and arrangement of parts may be resorted to without departing from the spirit and scope of the invention.

What is claimed is:

1. A cephalosporin compound represented by the following formula (I):

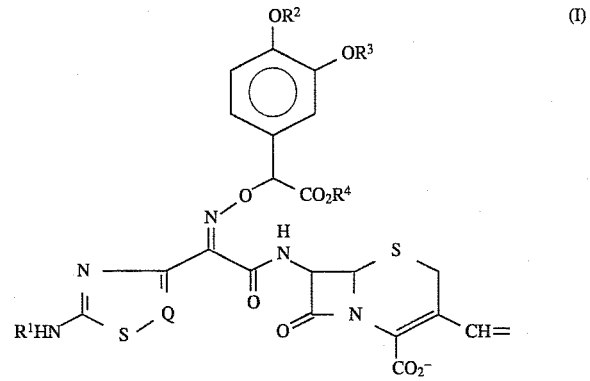

-continued

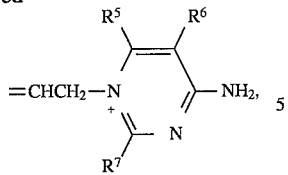

its pharmaceutically acceptable non-toxic salt, physiologically hydrolyzable ester, hydrate and solvate, and isomers thereof, in which $R^1$ and $R^4$ independently represent hydrogen, $R^2$ and $R^3$ are identical or different and independently represent hydrogen or acetyl, $R^5$, $R^6$ and $R^7$ are identical or different and independently represent hydrogen, amino, $C_{1-4}$ alkyl substituted amino, hydroxy, alkoxy, $C_{1-4}$ alkyl, carboxyl or alkoxycarbonyl, or $R^5$ and $R^6$ together with carbon atoms to which they are attached form a $C_{3-7}$ cycle, and Q represents CH or N.

2. The compound of formula (I) according to claim 1, wherein $R^5$ represents hydrogen or amino, and $R^6$ and $R^7$ independently of one another represent hydrogen, amino or methyl, or $R^5$ and $R^6$ together with the carbon atoms to which they are attached form a $C_5$ to $C_6$ cycle.

3. The compound of formula (I) according to claim 1, wherein the compound is selected from the group consisting of:

7-[(Z)-2-(2-aminothiazol-4-yl)-2-(α-carboxy-3,4-dihydroxybenzyloxyimino)acetamido]- 3-[(E)-3-(4,6-diaminopyrimidinium-1-yl)- 1-propen-1-yl]-3-cephem-4-carboxylate (R- and S-forms);

7-[(Z)-2-(2-aminothiazol-4-yl)-2-(α-carboxy-3,4-dihydroxybenzyloxyimino)acetamido]-3-[(E)-3-(4-aminopyrimidinium-1-yl)- 1-propen-1-yl]-3-cephem-4-carboxylate (R- and S-forms);

7-[(Z)-2-(2-aminothiazol-4-yl)-2-(α-carboxy-3,4-dihydroxybenzyloxyimino)acetamido]-3-[(E)-3-(4-amino-5,6-cyclopentanopyrimidinium- 1-yl)-1-propen-1-yl]-3-cephem-4-carboxylate (R- and S-forms);

7-[(Z)-2-(2-aminothiazol-4-yl)-2-(α-carboxy-3,4-dihydroxybenzyloxyimino)acetamido]-3-[(E)-3-(4,6-diamino-5-methylpyrimidinium- 1-yl)-1-propen-1-yl]-3-cephem-4-carboxylate (R- and S-forms); and 7-[(Z)-2-(2-aminothiazol-4-yl)-2-(α-carboxy-3,4-dihydroxybenzyloxyimino)acetamido]- 3-[(E)-3-(4,5,6-triaminopyrimidinium- 1-yl)-1-propen-1-yl]-3-cephem-4-carboxylate (R- and S-forms).

4. A pharmaceutical composition comprising a therapeutically effective amount of the compound of formula (I), its pharmaceutically acceptable non-toxic salt, physiologically hydrolyzable ester, hydrate or solvate as defined in anyone of claims 1 to 3, together with a pharmaceutically acceptable carrier, excipient or additive.

* * * * *